(12) United States Patent
Tietze

(10) Patent No.: US 10,286,188 B2
(45) Date of Patent: May 14, 2019

(54) CATHETER PUNCTURING DEVICE

(71) Applicant: Bernd Tietze, Adelsdorf (DE)

(72) Inventor: Bernd Tietze, Adelsdorf (DE)

( * ) Notice: Subject to any disclaimer, the term of this patent is extended or adjusted under 35 U.S.C. 154(b) by 329 days.

(21) Appl. No.: 14/770,034

(22) PCT Filed: Feb. 25, 2013

(86) PCT No.: PCT/IB2013/051516
§ 371 (c)(1),
(2) Date: Aug. 24, 2015

(87) PCT Pub. No.: WO2014/128535
PCT Pub. Date: Aug. 28, 2014

(65) Prior Publication Data
US 2016/0001046 A1    Jan. 7, 2016

(51) Int. Cl.
*A61M 25/06* (2006.01)
*A61M 25/00* (2006.01)

(52) U.S. Cl.
CPC .... *A61M 25/0668* (2013.01); *A61M 25/0618* (2013.01); *A61M 25/0097* (2013.01); *A61M 25/0693* (2013.01)

(58) Field of Classification Search
CPC .......... A61M 25/0097; A61M 25/0618; A61M 25/0668; A61M 25/0693; A61M 2025/067
See application file for complete search history.

(56) References Cited

U.S. PATENT DOCUMENTS

| | | | | | |
|---|---|---|---|---|---|
| 4,175,564 | A | * | 11/1979 | Kwak | A61M 25/0668 604/171 |
| 4,306,562 | A | * | 12/1981 | Osborne | A61M 25/0668 604/164.05 |
| 4,451,256 | A | * | 5/1984 | Weikl | A61M 25/0668 604/164.03 |
| 4,585,013 | A | * | 4/1986 | Harris | A61N 1/057 604/160 |
| 4,888,000 | A | * | 12/1989 | McQuilkin | A61M 25/0668 604/164.05 |

(Continued)

FOREIGN PATENT DOCUMENTS

| DE | 2340534 A1 | 2/1975 |
|---|---|---|
| EP | 2127692 A1 | 12/2009 |

(Continued)

OTHER PUBLICATIONS

International Search Report for Corresponding International PCT Application No. PCT/IB2013/051516, dated Nov. 7, 2013.

*Primary Examiner* — Quynh-Nhu H. Vu
(74) *Attorney, Agent, or Firm* — Hauptman Ham, LLP

(57) ABSTRACT

The invention relates to a catheter puncturing device for treating a patient during a medical treatment, said device structurally simplifying the placement of a catheter and reducing the number of required individual components of a catheter puncturing device. This is achieved by a catheter puncturing device according to the invention, said device being a closed single-piece system in which all the components required for the puncturing process are combined and provided in a housing. At the same time, the device allows the catheter to be released from the catheter puncturing device and to be uncovered using a handle after the catheter has been successfully introduced into the punctured vessel.

20 Claims, 2 Drawing Sheets

(56) References Cited

U.S. PATENT DOCUMENTS

Figure 1:
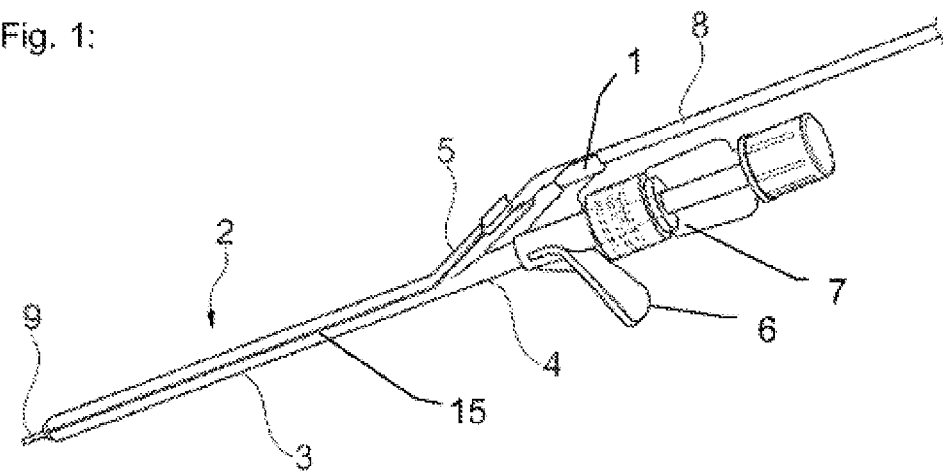

| | | | | |
|---|---|---|---|---|
| 5,195,978 A | * | 3/1993 | Schiffer | A61M 25/0169 |
| | | | | 604/161 |
| 5,697,914 A | * | 12/1997 | Brimhall | A61M 25/0637 |
| | | | | 604/164.01 |
| 6,585,703 B1 | * | 7/2003 | Kassel | A61M 25/0612 |
| | | | | 604/192 |
| 2008/0091137 A1 | * | 4/2008 | Reavill | A61M 25/01 |
| | | | | 604/27 |
| 2009/0292272 A1 | * | 11/2009 | McKinnon | A61M 25/0068 |
| | | | | 604/523 |
| 2010/0324490 A1 | * | 12/2010 | Pini | A61M 25/0668 |
| | | | | 604/167.03 |

FOREIGN PATENT DOCUMENTS

| | | |
|---|---|---|
| WO | 02/053045 A1 | 7/2002 |
| WO | 2010/111283 A1 | 9/2010 |

\* cited by examiner

CATHETER PUNCTURING DEVICE

The invention relates to a catheter puncture device according to the preamble of claim 1.

If a patient receiving medical care has to be fitted with a catheter, this is done by the medical personnel generally performing what is called the Seldinger technique. In a first step, the vessel (often an artery or vein) into which the catheter is to be inserted is punctured with a hollow puncture needle. Thereafter, a guide wire is pushed through the hollow puncture needle into the vessel. The hollow needle is then pulled back again over the guide wire lying inside it, such that the guide wire can be advanced farther into the punctured vessel in order to slightly widen this vessel initially using a dilator that is pushed over the guide wire. After removal of the dilator, the actual catheter is pushed over the guide wire into the vessel and is moved to the desired end position. The last step involves the guide wire being carefully pulled back out through the catheter.

Although this technique for puncturing blood vessels after Seldinger is a standard technique for the purpose of catheterization, fitting the catheter in place requires a large number of different maneuvers and instruments, which presuppose considerable experience in this area. Moreover, on account of various devices being pushed in and pulled out several times, there is a danger of articles or persons being contaminated by escaping blood. Finally, there is also the danger of an air embolism, i.e. if there is a slight underpressure in the punctured vessel. Therefore, as aids for catheterization, catheter puncture devices are known which are intended to permit simplified handling.

DE 101 00 102 discloses a catheter puncture device that simplifies the fitting of a catheter, since the implements needed for performing a puncture and for fitting a catheter are made available in a system composed of several parts, without the need for a guide wire or additional dilation devices.

The catheter puncture device disclosed therein comprises a tubular housing with an elongate housing portion which merges into an extension portion, and from which a branch portion branches off at an angle. The housing portion and the branch portion have a continuous lateral opening, which is closed by a flexible sheath which extends along the branch portion and the housing portion and into which a catheter can be pushed. During the puncturing of the vessel, the puncture needle extending along the elongate housing portion and the extension portion emerges from the tip of the housing and, after the puncture procedure, is pulled back into the housing to a location behind the branching site of the branch portion. A blood collection container is located at the rear end of the puncture needle.

The catheter is then inserted through the branch portion and the housing portion out of the housing through the flexible sheath into the punctured vessel, as far as the desired depth. Only then is the catheter puncture device withdrawn from the punctured vessel of the patient. Lastly, the flexible sheath is withdrawn from the housing or peeled off from the catheter via a lateral longitudinal slit. Therefore, after the puncture procedure has been performed with the catheter puncture device disclosed in DE 101 00 102, there are, in addition to the fitted catheter itself, a total of two other parts, on the one hand the housing with the puncture needle and with the blood collection container and, on the other hand, the detached sheath.

In addition to the above-described prior art, further catheterization methods are known that use a modified Seldinger technique, wherein some of the catheter puncture devices, always in multiple parts, work using what is called the peel-away technique, in which, after the catheter has been placed in the punctured vessel, the introducer sleeves divide into two parts at a peel-away point and can be withdrawn from the vessel without a movement of the catheter.

Against this background, the object of the present invention is to create a catheter puncture device which further structurally simplifies the placement of a catheter and further reduces the number of required individual components of the catheter puncture device.

This object is achieved by a catheter puncture device having the characterizing features of claim 1.

The dependent claims set forth advantageous embodiments of the invention.

The catheter puncture device according to the invention is a closed, one-piece system in which all the components required for the puncture procedure are combined and provided in a housing, and which at the same time allows the catheter to be released from the catheter puncture device and uncovered in one maneuver after the catheter has been introduced into the punctured vessel.

To develop it further now, the housing of the catheter puncture device according to the invention is formed only in one piece, wherein the elongate, tubular and closed housing portion guides a puncture needle, protruding with its tip from the elongate housing portion and extending along the elongate housing portion and the extension portion, and at the same time it also forms the guide channel for the catheter. After the vessel has been punctured by the puncture needle and the puncture needle has been returned to a point behind the branching site of the branch portion, the catheter can be inserted through the branch portion into the elongate housing portion, wherein at least one predetermined breaking point extends along the branch portion as far as the tip of the one-piece, elongate housing portion, which predetermined breaking point allows the housing to be opened, such that the catheter is exposed and the catheter puncture device can be removed.

Thus, within a single housing, the catheter puncture device according to the invention firstly comprises the puncture needle, which at one end is pushed out of the elongate housing portion and punctures the vessel. The end of the housing itself is also pushed slightly into the punctured vessel. Once the vessel is punctured, blood enters the puncture needle and is received in a preferably transparent blood collection container arranged at the other end of the puncture needle.

After the puncture has been performed, the puncture needle, with the blood collection container located thereon, is pulled back out of the vessel, with the housing itself remaining in the vessel.

The puncture needle is pulled back until the tip comes to lie behind the branching site of the branch portion of the housing and an abutment arranged on the puncture needle strikes a corresponding counterbearing in the housing, such that the puncture needle cannot be withdrawn completely from the catheter puncture device. Likewise, to safely prevent the puncture needle from being pushed in again, a blocking element secures the puncture needle, such that the tip thereof contaminated with blood comes to lie safely in the housing and does not pose a risk of injury to the medical personnel or other persons.

The catheter is then inserted through the branch portion and through the housing into the punctured vessel and is pushed to the desired depth into the vessel.

In the last step of the procedure, the two predetermined breaking points extending laterally on the branch portion and on the housing are now opened by means of a tear-open tab on the branch portion, and both halves of the housing portion are completely separated from each other.

The inserted catheter then lies uncovered, and the catheter puncture device according to the invention, along with the puncture needle and blood collection container, can be easily disposed of without risk of injury.

In an advantageous embodiment of the invention, the catheter, prior to being pushed into the punctured vessel, is releasably fixed on a holder additionally arranged on the housing. Here, a clamping holder is expediently provided which can be released with one hand. This ensures, on the one hand, that the flexible catheter does not get in the way during the actual puncturing procedure or does not come loose from the puncture device. On the other hand, however, after the puncturing procedure has been performed, said catheter can be easily released from the fixing holder and thus pushed into the punctured vessel.

In another advantageous embodiment of the invention, two approximately parallel predetermined breaking points are provided which extend along the branch portion as far as the tip of the housing. It is advantageous here that the distance between them defines the width of an opening strip removable from the housing, wherein this width corresponds approximately to that of the catheter that is to be exposed.

This ensures that the peeling-off of the opening strip exposes a slit-shaped opening over the entire guide length of the catheter in the housing, such that the catheter can be released from the housing without applying force. This is a considerable improvement in the sense that it is thus possible to reliably prevent a situation in which, during the release of the housing from the catheter that has been pushed into the vessel of the patient, the catheter is accidentally pulled back out of the vessel.

Moreover, for the removal of this opening strip, a tearing-open device of expedient design is arranged thereon in the area of the branch portion. This is advantageous in the sense that the opening of the housing along the predetermined breaking points takes place in the direction toward the punctured patient and not away from the latter. This again ensures that the inserted catheter is not accidentally pulled out of the vessel, since the pulling movement applied to the housing in order to remove the opening strip takes place toward the patient.

In an advantageous embodiment of the catheter puncture device, a tearing-open device is provided on the predetermined breaking point and is designed as a grip surface, at least on one side, for better introduction of tensile force into the predetermined breaking point. By taking hold of this protruding gripping surface, which is designed with a shape and size allowing it to be safely held between index finger and thumb for example, it is possible to safely introduce the force needed to overcome the break strength of the for example notched predetermined breaking point.

Figure 2:
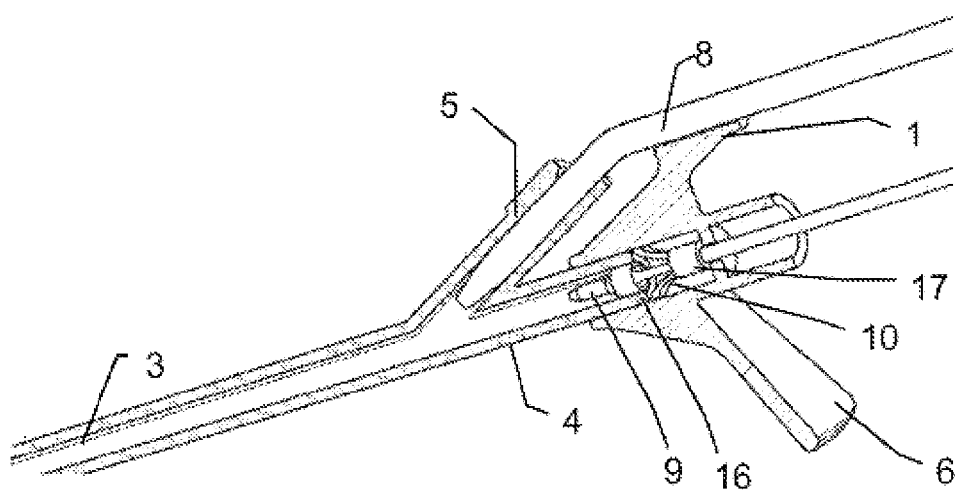
Figure 3:
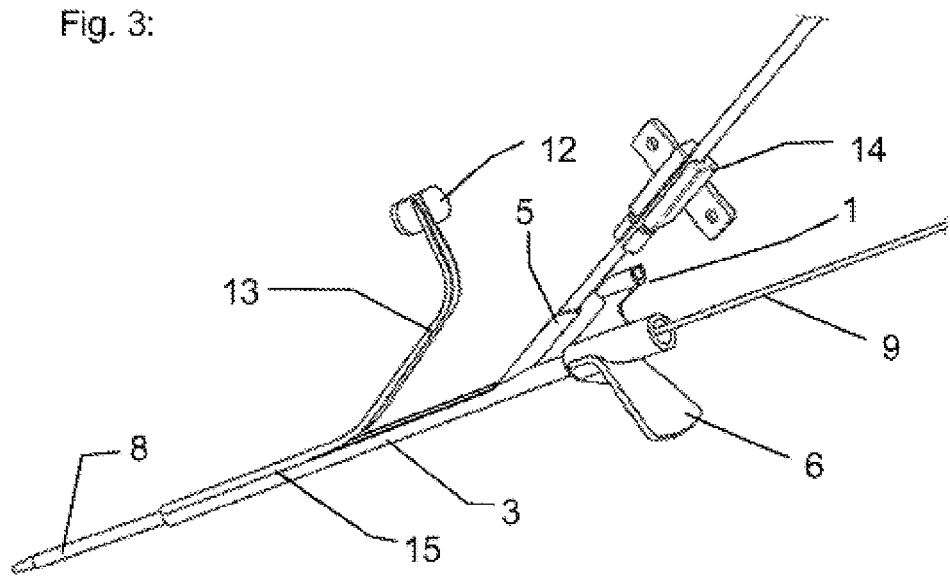
Figure 4:
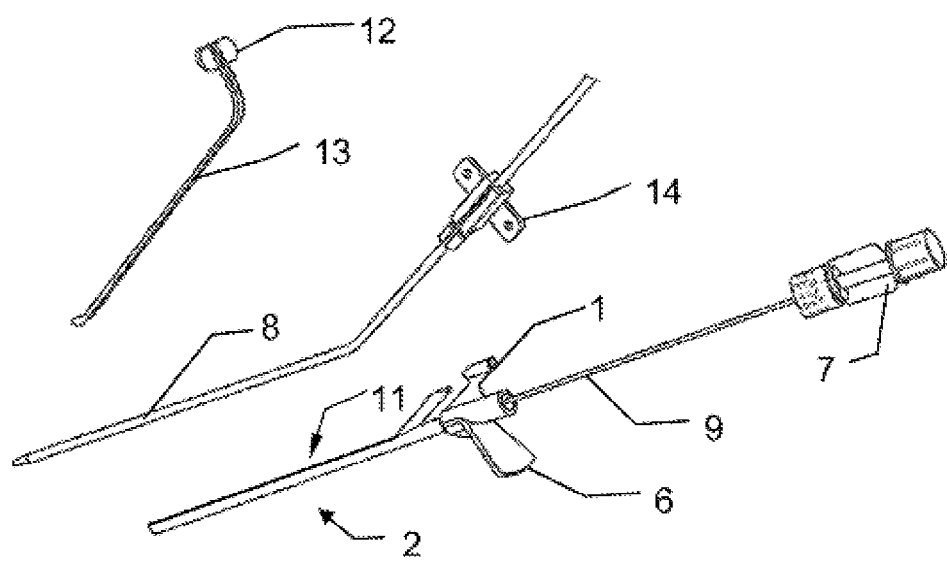

For the purpose of a closer description, an embodiment of the one-piece catheter puncture device according to the invention is shown in detail in FIGS. 1 to 4, in which FIG. 1 shows a perspective view of a catheter puncture device according to the invention, more or less in its original size, FIG. 2 shows an enlarged detail of a sectional view through the housing after the puncture has been performed, with the puncture needle pulled back, FIG. 3 shows a perspective view of the catheter puncture device during the opening of the predetermined breaking points, and FIG. 4 shows the device after the predetermined breaking points have been completely opened.

FIG. 1 shows the catheter puncture device 2 according to the invention, consisting of a tubular housing 3 with an elongate housing portion which merges into an extension portion for guiding the puncture needle 9 with blood collection container 7, abutment and blocking element 17, and from which a branch portion 5 branches off at an angle, through which branch portion 5 a catheter 8 can be pushed into the elongate housing portion. In terms of these design properties, the novel catheter puncture device follows the prior art.

In its outward appearance, the catheter puncture device 2 according to the invention is already considerably narrower than was the case of the designs cited in the prior art. This is achieved primarily by the fact that the predetermined breaking points 15, which can be discerned only on one side in the illustrated design, but which also extend in parallel on the not discernible rear face of the device in the concrete design solution, allow both the catheter 8 and also the cannula 9 for puncturing the vessel to be guided in the same tubular housing 3.

It should be mentioned here that the blood collection container 7, which is arranged on the rear housing portion 4 with handle 6 via a screw connection, does not necessarily have to be present in this illustrated design. Alternatively, the blood collection container 7 can also be replaced by a plugged-on disposable syringe, for example a 10-ml syringe, without thereby impairing the structural functionality. To this extent, the blood collection container 7, in the design solution illustrated here, represents only one possible design option. A blood collection container 7 is to be understood in principle as any body that can be fitted onto the catheter puncture device 2 and here prevents escape of blood during the puncture procedure.

Looking now at FIG. 2, which is a sectional view of the catheter puncture device 2 in the area of entry of the catheter 8 through the branch portion 5, this dual function of the tubular housing 3 of the catheter puncture device 2 becomes very clear. FIG. 2 shows the method step in which the catheter puncture device 2 has already been successfully inserted into a vessel of the patient, which is not illustrated here. After this puncture procedure, the cannula 8 can be pulled back to a point behind the branch portion 5 into a rear area 4 of the catheter puncture device 2, where locking takes place. This locking has the effect that this puncture needle 9 cannot be moved forward, nor can it be moved farther out from the device.

In the design according to the invention as shown in FIG. 2, this locking is obtained by means of an expansion body 17 whose catching arms 10 expand inside the tubular housing 3, after a step 16 has been passed, and they thus finally prevent the puncture needle 9 from being pushed forward. This locking effect cannot be canceled.

This expansion body 17 according to the invention with catching arms 10 is secured at the front on the puncture needle 9, the orientation of the catching arms 10 having the effect that a return movement of the puncture needle 9 is easily possible since, although the catching arms 10 bear on the inner jacket of the tubular housing 3, no blocking of the movement can take place in the pulling direction. Only after they have engaged in the corresponding housing step 16 can the catching arms 10 spread farther open and thus effect the locking.

FIG. 2 moreover shows the front end of the cannula 8 to be inserted, which cannula 8 is pushed into the branch portion 5 of the catheter puncture device 2. It will be clear from a comparison with FIG. 1 that the catheter 8 is fixed in this starting position by a holder 1, which fixes the catheter 8 in this position until it is to be inserted into the punctured vessel. For this purpose, provision is made that the catheter 8, when it is to be pushed in farther, can be pulled upward out of the clamping holder 1 and thus brought to a movable position. Since, after the puncture has been performed, the puncture needle 9 no longer blocks the tubular housing 3 as a guide for the catheter 8, an open guide channel is present through which the catheter 8 can now be inserted into the vessel of the patient.

FIG. 3 shows the procedure after the catheter 8 has been pushed into the punctured vessel of the patient. Since the catheter 8 is now in place, the tubular vessel 3 can be pulled out of the punctured vessel of the patient. However, the catheter 8 is still enclosed in the tubular housing 3 of the catheter puncture device 2 and first of all has to be released from it. For this purpose, provision is made for the detachment of an opening strip 13, which is defined by the two predetermined breaking points 15 that extend in the longitudinal direction from the branching site 5 to the tip of the tubular housing 3.

FIG. 3 shows the procedure of detaching this opening strip 13, as a result of which, as is shown in FIG. 4, the individual constituent parts of the catheter puncture device 2 are separated. After the opening strip 13 has been pulled off, the catheter puncture device 2, previously in one piece, disassembles into the actual inserted catheter 8, the catheter puncture device 2 with the puncture needle 9 drawn back completely as far as the abutment and with the elongate outlet opening 11 for the catheter, and the opening strip 13 which has exposed the corresponding opening 11.

It is clear here that the puncture needle 9 remains safely in the catheter puncture device 2, and also that the blood that has emerged during the puncture procedure remains safely in the blood collection container 7, without any risk of contamination of the personnel working with the catheter puncture device 2. To this extent, the present safety cannula with locking action meets the relevant requirements of the Medical Devices Act.

The detachment of the opening strip 13 on the parallel predetermined breaking points 15 along the tubular housing 3 is made easier by grip surfaces 12 in the area of the branch portion 5. These wing-like grip surfaces 12 branching off on both sides of the catheter puncture device 2 allow this area to be easily gripped, for example between thumb and index finger, as a result of which it is possible to further reduce the risk of the catheter 8, already located in the vessel, being pulled out accidentally.

The invention claimed is:

1. A catheter puncture device (2) comprising:
    a tubular housing (3) with an elongate housing portion and a rear portion, the catheter puncture device having a branch portion which branches off at an angle from the tubular housing, the catheter puncture device having a puncture needle at least partially within the tubular housing, the puncture needle having a tip, the rear portion is arranged for guiding the puncture needle (9), the puncture needle having a blood collection container (7) and an abutment and blocking element, and the branch portion (5) configured to receive a catheter (8) into the elongate housing portion, wherein the tubular housing (3) of the catheter puncture device (2) is in one piece, wherein the elongate, tubular housing portion is configured to guide the puncture needle (9), the puncture needle tip protruding from a front of the elongate housing portion and the puncture needle extending along the housing (3), and also form a guide channel for the catheter (8) which, after a puncture has been made and the puncture needle (9) has been returned to a point behind a branching of the branch portion (5), is to be inserted through the branch portion (5) into the elongate housing portion,
    wherein at least one predetermined breaking point (15) extends along the branch portion (5) as far as a tip of the elongate housing portion, which predetermined breaking point (15) is configured to allow the tubular housing (3) of the catheter puncture device (2) to be broken open in order to remove the housing (3) from the catheter (8) after the catheter (8) has been pushed through,
    wherein the abutment and blocking element comprises an expansion body (17) in a front portion of the puncture needle (9), the expansion body comprises catching arms and, when the puncture needle (9) is pulled back past the branch portion (5), the catching arms (10) of the expansion body (17) are configured to spread open past a step (16) in the rear portion (4) of the tubular housing (3) and lock the puncture needle.

2. The catheter puncture device as claimed in claim 1, wherein at least one holder (1) is arranged on the housing (3) and to releasably fix the catheter (8) in the branch portion (5) until said catheter (8) is pushed into the housing (3).

3. The catheter puncture device as claimed in claim 1, wherein the tip of the elongate housing portion, from which the puncture needle (9) is configured to emerge to perform the puncture, is rounded to a point.

4. The catheter puncture device as claimed in claim 1, wherein, after the puncture has been made, the puncture needle (9) is configured to be returned into the housing (3) only as far as the step in the rear portion, wherein the abutment and blocking element for preventing the puncture needle (9) from being pushed again into the housing (3) is arranged behind the branching of the branch portion (5).

5. The catheter puncture device as claimed in claim 1, wherein the at least one predetermined breaking point (15) is one or more grip surfaces (12) arranged thereon.

6. The catheter puncture device as claimed in claim 5, wherein the one or more grip surfaces (12) on the predetermined breaking point (15) is designed as at least one grip surface for better introduction of tensile force into the at least one predetermined breaking point (15).

7. The catheter puncture device as claimed in claim 1, wherein two approximately parallel predetermined breaking points (15) extend along the branch portion (5) as far as the tip of the housing (3), a distance between them defining [[the]] a width of an opening strip (13) removable from the housing (3), wherein this width corresponds approximately to that of the catheter (8) that is to be exposed.

8. A catheter puncture device comprising:
    a tubular housing extending in a first direction and having a branch portion in communication with the tubular housing, the branch portion branching off from the tubular housing in a second direction different from the first direction, the tubular housing extending in the first direction having a front portion and a rear portion, the branch portion configured to receive a catheter and to guide the received catheter into the front portion; and
    a puncture needle at least partially within the tubular housing and extending in the first direction toward the front portion, the puncture needle having one or more catching arms extending outward from the puncture needle, the one or more catching arms biased to expand in a direction away from the puncture needle, the catching arms configured to spread open away from the puncture needle after the catching arms are withdrawn from the rear portion of the tubular housing and to prevent movement of the puncture needle in the tubular housing toward the front portion after the catching arms are withdrawn from the rear portion of the tubular housing.

9. The catheter puncture device as claimed in claim 8, wherein the catheter puncture device further comprises at least one predetermined breaking point extending along the branch portion and the front portion, the at least one predetermined breaking point configured to allow the tubular housing to be broken open in order to remove the housing from the catheter after the catheter has been pushed through the housing.

10. The catheter puncture device as claimed in claim 8, wherein the catching arms are connected to a front portion of the puncture needle adjacent a tip of the puncture needle.

11. The catheter puncture device as claimed in claim 8, further comprising a handle portion surrounding at least a portion of the rear portion of the tubular housing, the handle having a through opening extending in the first direction and in communication with the tubular housing, the handle through opening having a first diameter greater than the tubular housing at a position adjacent the rear portion, the handle through opening having a second diameter smaller than the tubular housing at a position distant the rear portion.

12. The catheter puncture device as claimed in claim 11, wherein the puncture needle comprises an expansion body adjacent a tip of the puncture needle, the one or more catching arms attached to the expansion body, the expansion body having a diameter greater than the second diameter of the handle through opening.

13. The catheter puncture device as claimed in claim 12, wherein the expansion body diameter is smaller than the tubular housing.

14. The catheter puncture device as claimed in claim 8, wherein the puncture needle further comprises a blood collection container attached thereto.

15. A catheter puncture device (2) comprising:
a tubular housing and a puncture needle,
wherein the tubular housing is in one piece and of a closed design,
the tubular housing has an elongate housing portion, a branch portion, and an extension portion,
the elongate housing portion merges into the extension portion for guiding the puncture needle (9) in the tubular housing,
the puncture needle is configured to have a tip protrude from the front of the elongate housing portion,
the puncture needle has a blood collection container (7) and a blocking element,
the branch portion (5) branches off at an angle from the tubular housing,
the branch portion is configured to have a catheter (8) pushed into the elongate housing portion after a puncture has been made and the puncture needle (9) has been returned to a point behind the branching site of the branch portion (5),
wherein at least one predetermined breaking point (15) extends along the branch portion (5) as far as the tip of the elongate housing portion, the at least one predetermined breaking point (15) allows the tubular housing (3) of the catheter puncture device (2) to be broken open in order to remove the housing (3) from the catheter (8) after the catheter (8) has been pushed through, wherein the blocking element fixes the puncture needle (9) after the blocking element has been returned through the branching site of the branch portion (5),
wherein the blocking element is an expansion body (17) in the front portion of the puncture needle (9),
wherein the expansion body has catching arms and, when the puncture needle (9) is pulled back past the branch portion (5), the catching arms (10) of the expansion body (17) spread open into a step (16) in the rear area (4) of the tubular housing (3) and thus lock the puncture needle.

16. The catheter puncture device as claimed in claim 15, further comprising at least one holder arranged on the tubular housing and configured to releasably fix the catheter in the branch portion until the catheter is pushed into the housing.

17. The catheter puncture device as claimed in claim 15, wherein a tip of the elongate housing portion, from which the puncture needle is configured to emerge to perform a puncture, is rounded to a point.

18. The catheter puncture device as claimed in claim 15, wherein the at least one predetermined breaking point is one or more grip surfaces arranged thereon.

19. The catheter puncture device as claimed in claim 18, wherein the one or more grip surfaces on the predetermined breaking point is designed as at least one grip surface for better introduction of tensile force into the at least one predetermined breaking point.

20. The catheter puncture device as claimed in claim 15, wherein two approximately parallel predetermined breaking points extend along the branch portion as far as the tip of the housing, a distance between them defining a width of an opening strip removable from the housing, wherein this width corresponds approximately to that of the catheter that is to be exposed.

* * * * *